US00PP27867P2

(12) United States Plant Patent
Lewis

(10) Patent No.: US PP27,867 P2
(45) Date of Patent: Apr. 11, 2017

(54) GALA APPLE TREE NAMED 'BL-14'

(50) Latin Name: *Malus domestica*
Varietal Denomination: BL-14

(71) Applicant: Brandon Lewis, Wenatchee, WA (US)

(72) Inventor: Brandon Lewis, Wenatchee, WA (US)

( * ) Notice: Subject to any disclaimer, the term of this patent is extended or adjusted under 35 U.S.C. 154(b) by 0 days.

(21) Appl. No.: 14/998,806

(22) Filed: Feb. 18, 2016

(51) Int. Cl.
*A01H 5/08* (2006.01)

(52) U.S. Cl.
USPC ..... Plt./162

(58) Field of Classification Search
USPC ..... Plt./162
See application file for complete search history.

*Primary Examiner* — Annette Para
(74) *Attorney, Agent, or Firm* — Klarquist Sparkman, LLP

(57) ABSTRACT

A new and distinctive cultivar of *Malus domestica* 'apple', variety Gala, that is distinguished by the combination of the uniqueness of its fruit, bloom and harvest date differences.

6 Drawing Sheets

Latin name of the genus and species of the plant claimed: *Malus domestica.*

Variety denomination: 'BL-14'.

BACKGROUND OF THE INVENTION

In August 2010 while viewing the maturity development of apples in my 'Banning Gala' (U.S. Plant Pat. No. 13,753) apple tree orchard located at 18998 Marten Road, Quincy, Grant County, Wash. 98848, a limb mutation of advanced maturity and more intense color development was discovered on one of these trees. Trees were asexually propagated at my direction by budding on 'M9-RN29' rootstock (U.S. Plant Pat. No. 10,714) in the fall of 2011 and planted a cultivated area of my East Wenatchee, Wash. orchard in 2012. Fruit from these second generation trees were identical to those from the mother limb with respect to maturity dates and appearance.

Asexual reproduction of this new variety budded onto 'M9-RN29' rootstock in East Wenatchee, Wash. and observation of the resulting trees growing in East Wenatchee, Wash. has shown that the foregoing characteristics are firmly fixed and come true to type.

BRIEF SUMMARY OF THE INVENTION

'BL-14' Gala, as shown, exhibits a distinct early maturity date from other comparison Gala varieties grown in close proximity to 'BL-14', has an intense coloration and striping pattern in comparison to the other compared selections, and exhibits higher pH and lower acid levels than 'Gale Gala' (U.S. Plant Pat. No. 10,114), 'Banning Gala', and 'Simmons Gala' (U.S. Plant Pat. No. 10,840). Table 1 below contains a comparison of selected properties of 'BL-14' with some other gala varieties.

TABLE 1

Table comparing mature fruit indices of 'BL-14' Gala, 'Banning Gala', 'Gale Gala', 'Imperial' Gala (not patented), and 'Simmons Gala'.

| Variety | Harvest Date | Run Date | Pressure | Brix | pH | Acid* | Bloom Date |
|---|---|---|---|---|---|---|---|
| 'BL-14' | Aug. 8, 2015 | Aug. 9, 2015 | 18.1 | 12.5 | 3.94 | 2.89 | Apr. 18, 2015 |
| 'Banning Gala' | Aug. 17, 2015 | Aug. 18, 2015 | 17 | 14 | 3.84 | 3.40 | Apr. 17, 2015 |
| 'Gale Gala' | Aug. 19, 2015 | Aug. 20, 2015 | 20.8 | 15.8 | 3.74 | 4.28 | Apr. 16, 2015 |
| 'Imperial' Gala | Aug. 17, 2015 | Aug. 18, 2015 | 14.5 | 11 | 3.93 | 2.89 | Apr. 15, 2015 |
| 'Simmons Gala' | Aug. 11, 2015 | Aug. 12, 2015 | 17.7 | 13 | 3.81 | 3.11 | Apr. 20, 2015 |

*measured as g/L using 0.1M NaOH.

DETAILED DESCRIPTION

Figure 1:
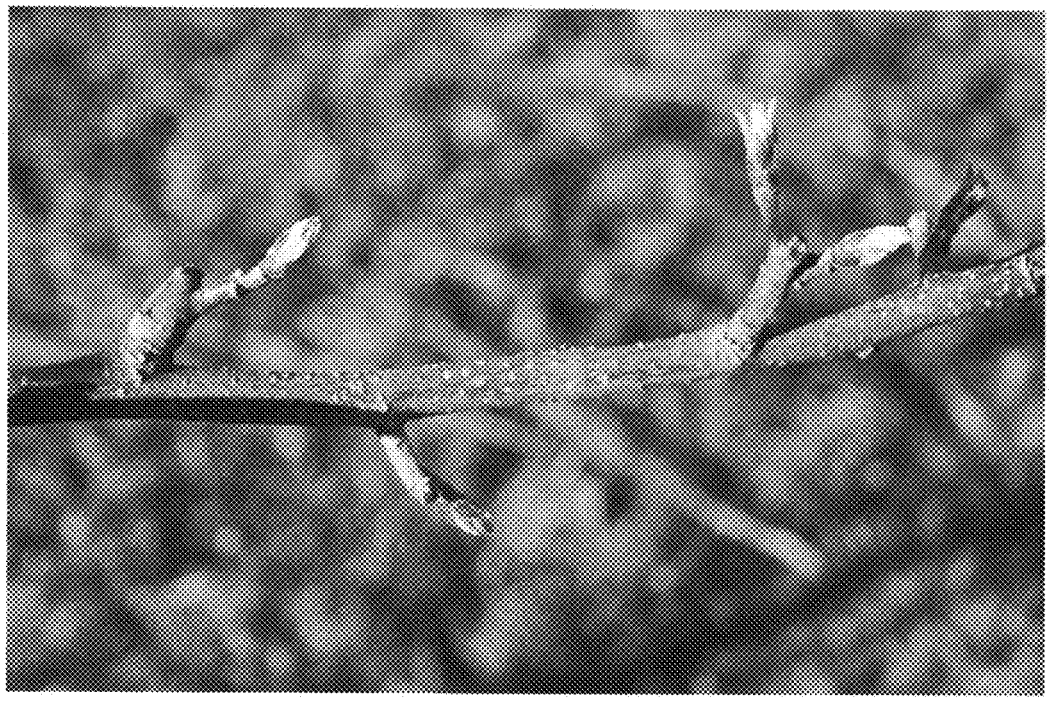
FIG. 1 is a view of typical spur development of my new variety at the green tip stage.
Figure 2:
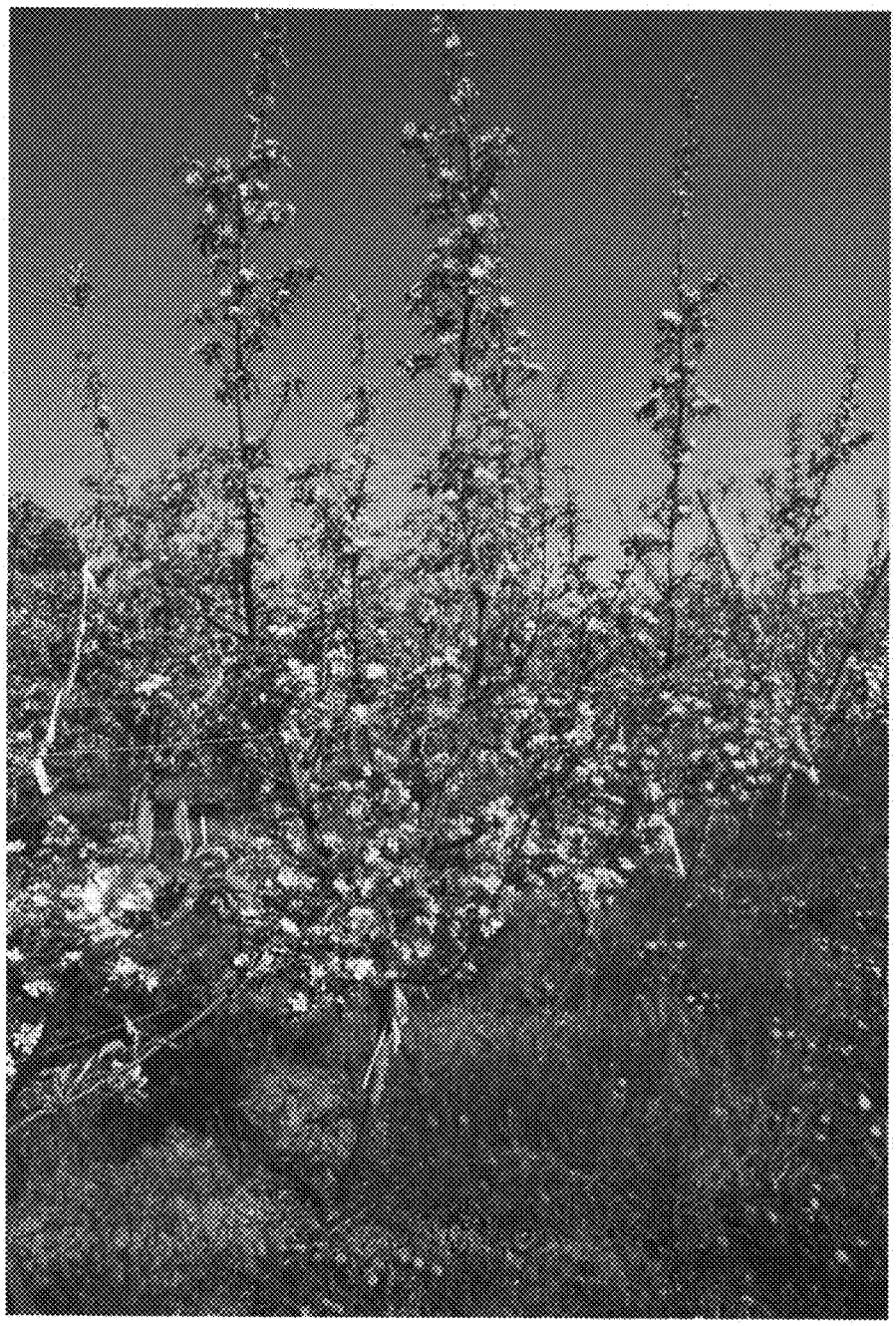
FIG. 2 is a view of a 'BL-14' second generation tree during bloom.
Figure 3:
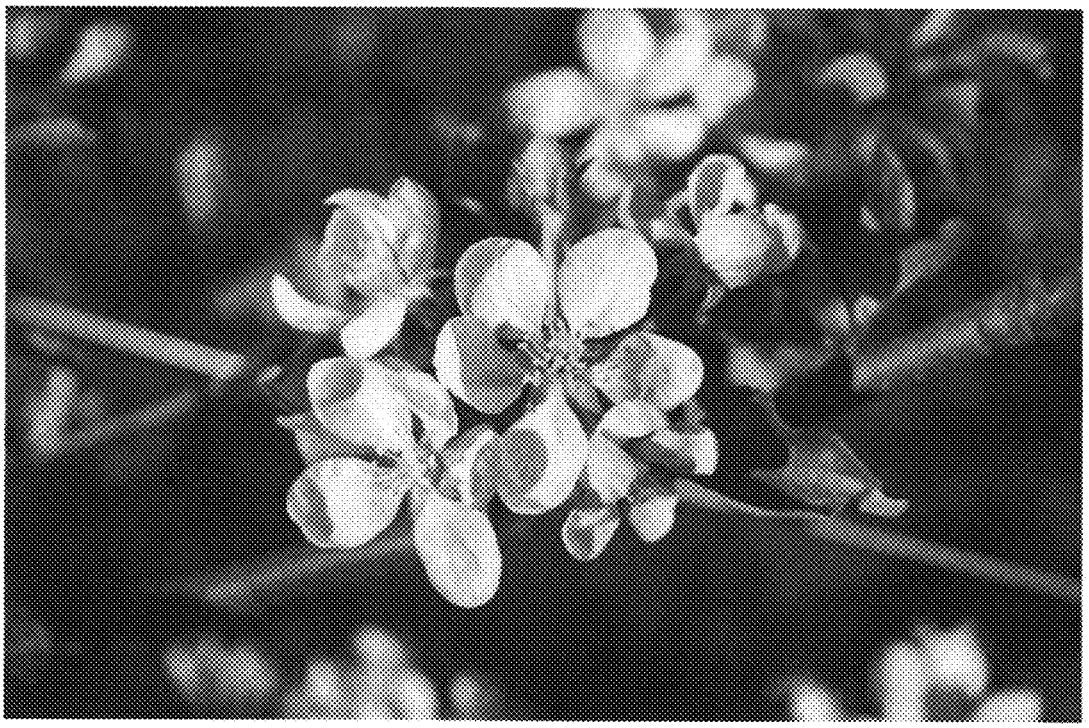
FIG. 3 is a close up view of blossoms of my new variety at 85% full bloom.
Figure 4:
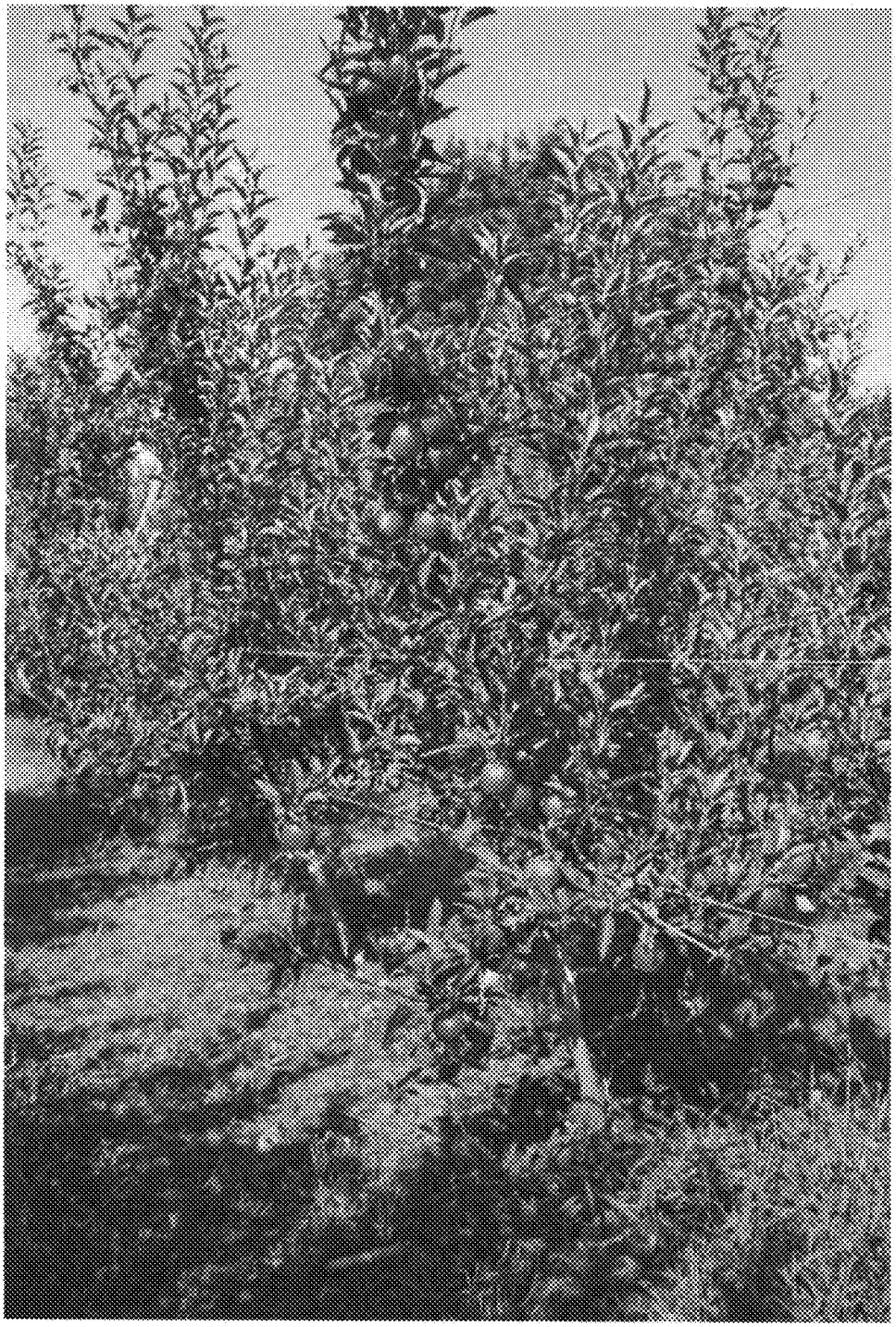
FIG. 4 is a view of a second generation 'BL-14' tree at harvest maturity.
Figure 5:
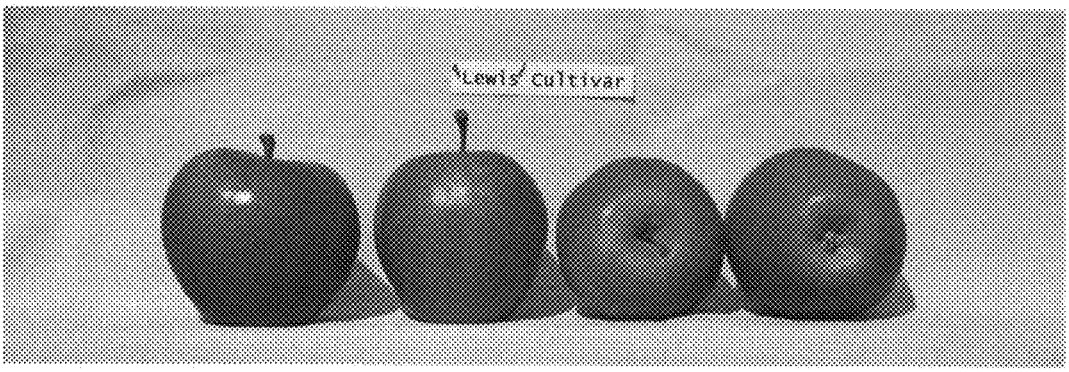
FIG. 5 is a view of harvested mature fruit from trees of the 'Lewis' cultivar (U.S. Plant Pat. No. 25,406).
Figure 6:
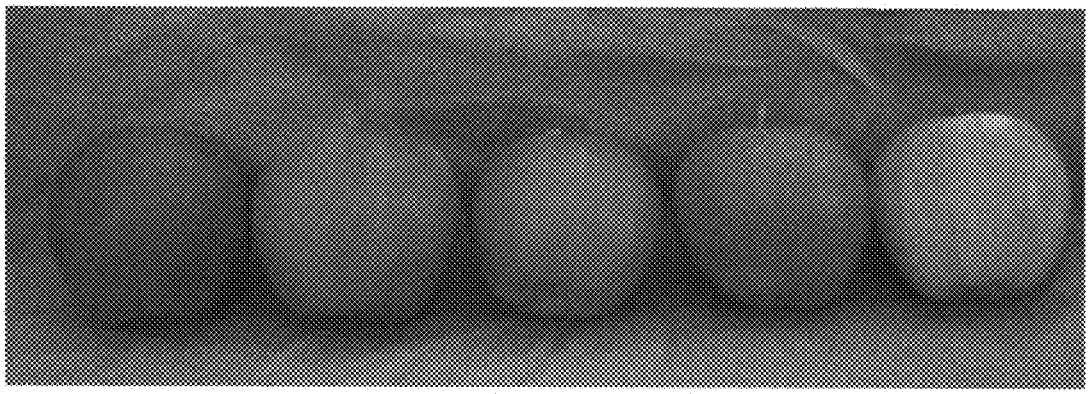
FIG. 6 is a view comparing mature fruit of my new 'BL-14' variety with, 'Banning Gala', 'Gale Gala', 'Simmons Gala' and 'Imperial' Gala (unpatented) fruit.

The observations below are from a typical 4th leaf second generation tree growing on 'N9-RN29' rootstock and at the Lewis orchard, 2820 Grant Rd, East Wenatchee, Douglas County, Wash., USDA hardiness zone 6b. All color references are from The R.H.S. colour chart by The Royal Horticultural Society copyright 2001 edition).

Tree:

*Type*.—Spur type with single buds per spur. Training is of the slender spindle type. The new 'BL-14' tree is a consistent bearer with moderate spur development.

*Vigor*.—Moderate.

*Overall shape*.—Upright and spreading as trained to slender spindle.

*Height*.—10 feet.

*Width*.—5 feet.

*Hardiness*.—Hardy for the Wenatchee, Wash. region.

*Productivity*.—Moderately heavy with yields of about 32 pounds from $4^{th}$ leaf trees on 'N9-RN29' rootstock in Wenatchee, Wash.; and expected to be about 48 to 52 pounds per tree in $6^{th}$ leaf.

Trunk:

*Size*.—Diameter at a height of 30 cm above graft union is 3.9 cm.

*Bark texture*.—Smooth.

*Bark color*.—From the grey-brown group N199A.

*Lenticels*.—Present and numerous in number averaging twelve per 4 $cm^2$. Average width is 1.5 mm, average length is 4.5 mm.

*Lenticels color*.—From the greyed-orange group 175D in the centers with the margins from the orange-white group 159A.

Branches:

*First year branches*.—Diameter: At mid-point of growth averages 6.5 mm with a range of 4.8 to 9.6 mm. Length: Averages 55.2 cm with a range of 30.5 to 81.0 cm. Color: From the brown group 200C. Lenticels: Are numerous averaging 14 per running cm of growth, are oval in shape and range from 0.8-0.9×1.3-1.5 mm. Color is from the white group 155B. Branch pubescence: Moderate in density covering 100% of surface area. Color from the white group 155C. Internodes: Distance between nodes ranges from 28.3 mm to 39.8 mm with an average of 34.3 mm.

*Two year old fruiting branches*.—Diameter: At mid-point of growth averages 6.3 mm ranging from 4.4 to 8.6 mm. Bark color is from the grey-brown group N199C. Spur development: Moderate. Spurs range in length from 2.8 mm to 8.5 mm in length with an average of 5.2 mm. Will tip bear. Lenticels: Few, averaging 5 per running cm and are round being 1.4 to 1.7 mm in diameter. Buds: Length ranges from 8.0 mm to 11.2 mm with an average of 9.6 mm. Diameter ranges from 4.3 mm to 5.6 mm with an average of 4.8 mm. Scale color is from the greyed-purple group 184B. Light scale pubescence observed, color from the white group 155B.

*Scaffold branches*.—Size: Ranges from 14.8 mm to 20.7 mm in diameter as measured 3 cm from trunk. Angle: As trained is moderate to flat - ranging from 75 to 90 degrees from vertical. Color: Color is from the grey-brown group 199A. Lenticels: Numerous in number, averaging 7 per 4 $cm^2$. Shape and size: Oval, ranging from 0.9 mm to 1.9 mm in width and 1.7 mm to 1.9 mm in length. Lenticels color: Color is from the yellow-white group 158D.

Leaves:

*Shape*.—Acute and upward folding.

*Texture*.—Upper surface leathery and undulating. Lower surface smooth with veins protruding.

*Sheen*.—High sheen on upper surface.

*Pubescence*.—Present on lower surface only, fine and moderate in density over 100% and color is from the white group 155B.

*Length*.—Blade length ranges from 8.2 cm to 10.3 cm with an average of 10.1 cm.

*Width*.—Ranging from 4.3 cm to 6.0 cm with an average of 5.1 cm.

*Margin*.—Considered serrate, with an occasional bi-serrate.

*Tip*.—Acuminate.

*Base*.—Rounded.

*Stipules*.—Present, 2 on all leaves. Shape: Subulate — Length ranges from 9.1 to 14.5 mm with an average of 12.2 mm; Width ranges from 0.8 to 2.0 mm with an average of 1.5 mm. Color: Is from the yellow-green group 147A. Pubescence: Is present on 100% of the lower surface only, light in quantity, and color from the white group 155B.

*Leaf color*.—Upper surface from the yellow-green group 147A; Lower surface from the yellow-green group 147B.

*Mid-vein*.—Prominent with considerable downiness over entire under surface. Pubescence color from white group 155A. Width at mid blade averages 1.7 mm. Under and upper surface vein color is from the yellow-green group 145C.

Petiole:

*Length*.—Ranges from 25.5 to 33.7 mm with an average of 28.5 mm. Shallow grove running the entire length.

*Diameter*.—Ranges from 2.0 mm to 2.4 mm with an average of 2.2 mm.

*Color*.—Upper and lower surface color from the yellow-green group 145C; Basal end high-lighted from the greyed-purple group 185A; Upper surface groove color from the yellow-green group 185C.

*Pubescence*.—Abundant with moderatc density over the entire length and circumference and the color is from the white group 155D.

Flowers: Full bloom date was Apr. 18, 2015 with 2 year average being April 24; number of blossoms per bud ranges from 5-6 mostly 6.

*Size*.—Considered medium in size. Diameter ranges from 37.7 to 47.9 mm when fully open with an average of 43.5 mm.

*Petal*.—Five in number. Shape is oblong and cupped inward with tip rolled upward and inward. Base is rounded and apex is rounded. Width averages 12.3 mm; length averages 19.4 mm. Color: background color is white (20%), overcolor both upper and lower surfaces is variable in the red-purple group 62D and 63A.

*Stamen*.—Number ranges from 19 to 20, mostly 20.

*Filament*.—Length ranges from 3.0 to 9.0 mm with an average of 6.2 mm. Color is from the yellow group 2C with a basal highlight from the red group 48A.

*Anthers*.—Kidney shaped that average 1.7 mm wide× 2.2 mm long. Color is from the greyed-yellow group 162D. Pollen is considered moderate in abundance with color from the greyed-yellow group 162D.

Pistil:

*Style*.—Length ranges from 10.4 mm to 13.7 mm with an average of 12.5 mm. Fused an average of 5.6 mm from base. Color is from the yellow-green group 145A. Pubescence is light at the base and color is white group 155B.

*Stigma*.—Clubshaped. Color is from the yellow-green group 153A.

*Sepals*.—5 per blossom. Shape is considered thin lanceolate with the tip being acuminate and the base being truncate. Average length is 9.4 mm and average width is 4.5 mm. Sepal color upper surface is from the yellow-green group 146B, sepal lower surface color from the yellow-green group 146D. Abundant pubescence is present on both 100% of the upper and lower surfaces with color from the white group 155B.

*Peduncle*.—Length ranges from 19.1 mm to 30.8 mm with an average of 25.9 mm. Diameter ranges from 1.0 mm to 1.2 mm with an average of 1.1 mm. Color is from the yellow-green group 148A. Considerable white downiness present over the entire surface with color from the green-white group 155B.

*Thalamus depth*.—ranges from 3.9 to 4.6 mm with an average of 4.0 mm.

Fruit: Observations and testing from second generation tree fruit.

*Form*.—Round conical. Equatorial diameter cross section is mostly regular. Exhibits mild lopsidedness with 5 crowns lightly pronounced.

*Size*.—Medium with a normal crop level. Averaging 7.6 cm in equatorial diameter and 6.9 cm in axis diameter.

*Stem*.—Long and medium in thickness. Length ranges from 26.3 mm to 38.1 mm with an average of 32 mm. Diameter ranges from 2.0 mm to 3.1 mm with an average of 2.7 mm. Exhibits moderate clubbing. No pubescence. Color from the grey-brown group N199D.

*Stem cavity*.—Average width is 27.9 mm and average depth is 16.1 mm.

*Cavity shape*.—Cone shaped.

*Lipped*.—No.

*Russet*.—No.

*Basin cavity*.—Is lightly ribbed and sides considered sloping. Average width is 24.8 mm and average depth is 8.7 mm.

*Eye*.—Erect convergent; Light white downiness covering 100%; Eye sepal color is from the yellow-green group 146C.

*Skin*.—Appearance: Washed in appearance (over 95% of surface area) and smooth, with over stripping of 30-50% of surface area. Wash under color from the red group 47A, stripe over color from the red group 46A.

*Thickness*.—Thin, 0.5 mm in thickness.

*Texture*.—On the brittle but somewhat tough side.

*Lenticels*.—Present, prominent and evenly distributed; averaging 8/cm$^2$; round with size ranging from 1.3 to 1.5 mm in diameter; color is from the white group 155D.

Core:

*Core position*.—Distant.

*Core line position*.—Basal meeting.

*Shape*.—Flat conical.

*Length*.—Ranges from 23.9 mm to 27.7 mm with an average of 25.6 mm.

*Diameter*.—Ranges from 34.1 mm to 40.7 mm with an average of 36.8 mm.

*Cell*.—Tufted: no. Cell Shape: elliptical. Length averages 16.1 mm, width averages 9.8 mm, wall to wall depth averages 6.3 mm.

*Tube*.—Cone shaped.

*Stamen position*.—Median.

*Axis*.—Is axile and open.

*Seed*.—Number: 1-3, mostly 2. Shape: Mostly obtuse with occasional acute; Length averages 8.4 mm; Width averages 4.6 mm. Color: From the greyed-orange group 177A.

*Flesh*.—Crisp, firm, melting, juicy and mildly subacid. Flavor is apple like. Browning noted 10-15 minutes following cutting. Color is from the white group 155A.

*Aroma*.—Mild, apple like.

*Date of harvest maturity*.—Aug. 8, 2015.

*Maturity indices*.—(Averages).

*Starch*.—Averages 3.5.

*Pressure*.—20.1.

*Soluble solids*.—12.0.

*Keeping quality*.—Good. Up to four months in common storage.

Pollination: Any diploid apple of the same bloom season.

Use: Desert. Excellent eating quality that is snappy, juicy, sweet with a very good mild acid balance with a melting skin.

Disease and insect resistance: Is considered to be susceptible to all insects and diseases found in the region of Central Washington. Fruit does not exhibit any physiological disorders on the tree nor during storage for the duration of normal storage lengths.

I claim:

1. A new and distinct apple tree cultivar of the variety Gala named 'BL-14' as herein illustrated and described.

* * * * *

'BL-14' Gala 'Banning Gala' 'Gale Gala' 'Simmons Gala' 'Imperial' Gala